(12) United States Patent
Kreuder

(10) Patent No.: US 10,138,154 B2
(45) Date of Patent: Nov. 27, 2018

(54) METHOD FOR PRODUCING A DENTAL PROSTHESIS

(71) Applicant: DENTSPLY International Inc., York, PA (US)

(72) Inventor: Peter Kreuder, Bad Nauheim (DE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 14/718,207

(22) Filed: May 21, 2015

(65) Prior Publication Data
US 2016/0340225 A1    Nov. 24, 2016

(51) Int. Cl.
| | | |
|---|---|---|
| C03B 32/02 | (2006.01) |
| C03C 10/00 | (2006.01) |
| C03B 19/04 | (2006.01) |
| C03B 19/10 | (2006.01) |
| C03B 19/02 | (2006.01) |
| A61K 6/027 | (2006.01) |
| C03C 3/097 | (2006.01) |

(52) U.S. Cl.
CPC ............ C03B 32/02 (2013.01); A61K 6/0273 (2013.01); A61K 6/0276 (2013.01); C03B 19/02 (2013.01); C03B 19/04 (2013.01); C03B 19/1055 (2013.01); C03C 3/097 (2013.01); C03C 10/0027 (2013.01)

(58) Field of Classification Search
CPC ........ A61K 6/027; C03B 32/02; C03B 19/02; C03C 10/0054; C03C 10/0027; C03C 10/0018
USPC ......................................................... 65/21.1
See application file for complete search history.

(56) References Cited

U.S. PATENT DOCUMENTS

| | | | |
|---|---|---|---|
| 4,431,420 A * | 2/1984 | Adair ........................ | A61C 3/00 106/35 |
| 4,515,634 A | 5/1985 | Wu et al. | |
| 4,789,649 A * | 12/1988 | Abert ..................... | A61L 27/105 106/35 |
| 5,507,981 A * | 4/1996 | Petticrew ............... | A61C 13/20 264/16 |
| 5,698,482 A | 12/1997 | Frank et al. | |
| 5,925,180 A | 7/1999 | Martin et al. | |
| 8,557,150 B2 | 10/2013 | Ritzberger et al. | |
| 2012/0248642 A1 | 10/2012 | Ritzberger et al. | |

FOREIGN PATENT DOCUMENTS

| | | |
|---|---|---|
| DE | 2651842 A1 | 5/1978 |
| DE | 29 49 619 | 11/1980 |
| DE | 3117470 C1 | 11/1982 |
| DE | 102009060274 A1 | 6/2011 |
| DE | 102010050275 A1 | 5/2012 |
| EP | 0225279 A1 | 12/1989 |
| EP | 1 484 031 B1 | 1/2007 |
| JP | 5649145 A | 5/1981 |
| JP | 6028911 A | 2/1985 |
| JP | 62108750 A | 5/1987 |
| JP | 62123042 A | 6/1987 |
| JP | 02045048 A | 2/1990 |
| JP | 0840744 A | 2/1996 |
| JP | 09501092 A | 2/1997 |
| JP | 2005053776 A | 3/2005 |
| JP | 2005187436 A | 7/2005 |
| JP | 2006089502 A | 4/2006 |
| JP | 2007190215 A | 8/2007 |
| JP | 2011225441 A | 11/2011 |
| RU | 2144814 C1 | 1/2000 |
| WO | 2009126317 A1 | 10/2009 |
| WO | 2011076422 A1 | 6/2011 |
| WO | 2012/059143 A1 | 5/2012 |

OTHER PUBLICATIONS

Written Opinion of International Application No. PCT/EP2013/074634 dated Mar. 28, 2014 (English translation).
International Preliminary Report on Patentability of International Application No. PCT/EP2013/074634 dated Sep. 29, 2014 (English translation).

\* cited by examiner

Primary Examiner — Mark Halpern
(74) Attorney, Agent, or Firm — Dentsply Sirona Inc.

(57) ABSTRACT

A method for producing a dental prosthesis based on lithium silicate glass or lithium silicate glass-ceramic, including the steps of: melting a powder mixture containing at least $SiO_2$, $Li_2O$, $Al_2O_3$; producing spherical, lens-shaped or rod-shaped glass particles solidified from the melt; portioning the glass particles and filling them into a crucible; melting the glass particles in the crucible and setting a viscosity v, wherein $4 \text{ dPa·s} \leq v \leq 80 \text{ dPa·s}$; casting the thus produced melt into a negative mold which is enclosed by an embedding compound and corresponds to the dental prosthesis and; solidifying the melt in the negative mold, and crystallizing lithium metasilicate and/or lithium disilicate from the solidified melt.

16 Claims, 2 Drawing Sheets

METHOD FOR PRODUCING A DENTAL PROSTHESIS

CROSS-REFERENCE TO RELATED APPLICATIONS

This is a national phase patent application of international application PCT/EP2013/074634, filed on Nov. 25, 2013, which claims the benefit of and priority to DE Application Ser No. 102012111683.0, filed on Nov. 30, 2012, which are herein incorporated by reference for all purposes.

FIELD OF THE INVENTION

The invention relates to a method for producing a dental prosthesis based on lithium silicate glass or lithium silicate glass-ceramic.

BACKGROUND OF THE INVENTION

To produce dental prosthesis based on lithium silicate glass-ceramic, it is known to produce cylindrical pellets and to subsequently grout them in a muffle (see, for instance, EP-B-1 484 031). This is a proven and accepted method, although also suggestions are known, according to which a lithium silicate glass melt is cast, as can be learned from U.S. Pat. No. 4,515,634.

In DE-A-29 49 619, it is described that a lithium silicate-based melt can be cast to produce a dental restoration. The glass does not contain $P_2O_5$.

For producing a lithium silicate-based precursor, U.S. Pat. No. 5,698,482 suggests to produce pellets by casting or uniaxial or isostatic pressing.

DE-A-10 2009 060 274 as well as WO-A-2012/059143 teach methods to produce a dental prosthesis from lithium disilicate glass-ceramic.

U.S. Pat. No. 5,507,981 teaches a method to produce a dental prosthesis, in the course of which a ceramic melt is fed to a negative mold by means of vacuum and pressure. A method to produce lithium silicate glasses or lithium silicate glass-ceramics is known from DE-A-10 2010 050 275.

The present invention is based on the problem to develop a method of the aforementioned type so that reproducible dental prosthesis can be produced by casting based on lithium silicate glass and lithium silicate glass-ceramic, respectively. In contrast to the prior art, simplified manufacturing techniques shall be given. Also, a starting material should be provided that can be managed without problems.

SUMMARY OF THE INVENTION

The present invention seeks to improve upon prior lithium silicate materials by providing an improved method for producing a dental prosthesis based on lithium silicate glass or lithium silicate glass-ceramic. In one aspect, the present invention provides a method for producing a dental prosthesis based on lithium silicate glass or lithium silicate glass-ceramic, comprising the steps of:

(a) melting a powder with the composition in wt-%

| | |
|---|---|
| $SiO_2$ | 50-70%; |
| $Li_2O$ | 5-25%; |
| $Al_2O_3$ | 0.1-20%; |
| $K_2O$ | 0.1-15%; |
| $CeO_2$ | 0.1-15%; |
| $B_2O_3$ | 0-5%; |
| $P_2O_5$ | 0-15%; |
| $Tb_2O_3$ | 0-2%; |
| $ZrO_2$ | 0-15%; |
| $ZnO$ | 0-4%; | and at least one additive between 0.1 and 5 wt-%, the additive being selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$, (b) producing spherical or lens-shaped glass particles solidified from the melt;

(c) portioning the glass particles and filling them into a crucible;

(d) melting the glass particles in the crucible and setting a viscosity v, wherein 4 dPa·s≤v≤80 dPa·s;

(e) casting the thus produced melt into a negative mold which is enclosed by an embedding compound and corresponds to the dental prosthesis to be produced;

(f) solidifying the melt in the negative mold; and (g) crystallizing lithium metasilicate as main crystalline phase from the solidified melt by employing a first heat treatment at a temperature between 600° C. and 760° C. over a time between 20 min and 120 min, wherein the heat treatment of the solidified melt takes place either in the negative mold or after removal from the negative mold.

In another aspect, the present invention contemplates a method for producing a dental prosthesis based on lithium silicate glass or lithium silicate glass-ceramic comprising the steps of:

(a) melting the powder mixture containing at least $SiO_2$, $Li_2O$, $Al_2O_3$, and (b) casting the thus produced melt into a negative mold which is enclosed by an embedding compound and corresponds to the dental prosthesis to be produced, wherein the dental prosthesis is produced using centrifugal casting or vacuum die-casting from a melt with the composition in wt-%

| | |
|---|---|
| $SiO_2$ | 50-70%; |
| $Li_2O$ | 5-25%; |
| $Al_2O_3$ | 0.1-20%; |
| $K_2O$ | 0.1-15%; |
| $CeO_2$ | 0.1-15%; |
| $B_2O_3$ | 0-5%; |
| $P_2O_5$ | 0-15%; |
| $Tb_2O_3$ | 0-2%; |
| $ZrO_2$ | 0-15%; |
| $ZnO$ | 0-4%; | and 0.1% and 5% of at least one additive selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$ In yet another aspect, any of the aspects of the present invention may be further characterized by one or any combination of the following features: further comprising the step of crystallizing lithium disilicate as main crystalline phase in a second heat treatment at a temperature between 760° C. and 860° C. over a time between 5 min and 60 min; wherein the dental prosthesis is produced by centrifugal casting or vacuum die-casting; wherein the melt is cast with a viscosity v, wherein 9 dPa·s to 40 dPa·s; wherein the melt further comprises at least one oxide of a transition metal with an atomic number between 41 and 79, such as Nb, Ta, and La, with a wt-% proportion between 0% and 8%, wherein the wt-% proportion of an oxide of the transition metals with the atomic number 59, 62, 64, 68 is at most 5%; wherein the dental prosthesis is produced from a melt with the composition in wt-%:

| | |
|---|---|
| $SiO_2$ | 55-65%; |
| $Li_2O$ | 10-20%; |
| $Al_2O_3$ | 0.2-15%; |
| $K_2O$ | 0.2-10%; |
| $CeO_2$ | 0.1-10%; |
| $B_2O_3$ | 0-5%; |
| $P_2O_5$ | 1-10%; |
| $Tb_2O_3$ | 0-2%; |
| $ZrO_2$ | 2-15%; |
| ZnO | 0-2%; | and
at least one additive between 0.1 and 5%, the additive being selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$; wherein the melt contains at least one oxide of a transition metal with an atomic number between 41 and 79, such as La, Nb, and Ta, with a wt-% proportion between 0% and 8%, wherein the wt-% proportion of an oxide of the transition metals with the atomic number 59, 62, 64, 68 is at most 5%; wherein the dental prosthesis is produced from a melt with the composition in wt-%:

| | |
|---|---|
| $SiO_2$ | 57-63%; |
| $Li_2O$ | 11-19%; |
| $Al_2O_3$ | 0.5-10%; |
| $K_2O$ | 0.5-10%; |
| $CeO_2$ | 0.1-10%; |
| $B_2O_3$ | 0-5%; |
| $P_2O_5$ | 1-10%; |
| $Tb_2O_3$ | 0-2%; |
| $ZrO_2$ | 4-15%; |
| ZnO | 0-2%; | and
at least one additive between 0.1% and 5%, the additive selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$; wherein the composition contains at least one oxide of a transition metal with an atomic number between 41 and 79, such as La, Nb, and Ta, with a wt-% proportion between 0% and 6%, wherein the wt-% proportion of an oxide of the transition metals with the atomic number 59, 62, 64, 68 is at most 5%; wherein the dental prosthesis is produced from a melt with the composition in wt-%:

| | |
|---|---|
| $SiO_2$ | 58-62% |
| $Li_2O$ | 13-19% |
| $Al_2O_3$ | 1-6% |
| $K_2O$ | 1-5% |
| $CeO_2$ | 0.1-5% |
| $B_2O_3$ | 0-4% |
| $P_2O_5$ | 2-8% |
| $Tb_2O_3$ | 0-2% |
| $ZrO_2$ | 8-12% |
| ZnO | 0-1% | at least one additive between 0.1 and 4%, the additive being selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, V2O5, and $Y_2O_3$; wherein the composition additionally contains at least one oxide of a transition metal with an atomic number between 41 and 79, such as La, Nb, and Ta, with a wt-% proportion between 0% and 5%, wherein the wt-% proportion of an oxide of the transition metals with the atomic number 59, 62, 64, 68 is at most 4%; wherein the melted powder is transformed into droplets by means of a nozzle, that the droplets are falling through a cooling section, in which at least a superficial solidification of the droplets takes place, that after falling through the cooling section the droplets are collected by a receptacle containing a liquid or a high temperature cotton, if necessary after quenching them beforehand; wherein for quenching, the droplets fall onto a metal substrate, the temperature of which is set between room temperature and 500° C.; wherein the powder mixture is melted over a time t1, wherein 4 h≤t1≤12 h at a temperature T1, wherein 1500° C.≤T1≤1600° C.; wherein during the transformation of the droplets, the nozzle is set to a temperature T2, wherein 1250° C.≤T2≤1450° C.; wherein during the transformation of the droplets, the nozzle is caused to vibrate at a frequency between 40 Hz and 60 Hz; wherein over a time t3, wherein 2 h≤t3≤6 h, the collected droplets are cooled down from a temperature T3, wherein 350° C.≤T3≤500° C. to room temperature to reduce internal stress; wherein after the second heat treatment, the cast is cooled down to room temperature over a time t7, wherein 10 min≤t7≤180 min; wherein a gypsum-bound embedding compound is used as an embedding compound; wherein the droplets are melted in a crucible or ladle made of graphite or ceramic; wherein when a graphite crucible is used, it is at least coated at the inside; wherein the melt is fed to the negative mold with a temperature T8, wherein 1200° C.≤T8≤1300° C.; wherein when casting the melt, the embedding compound is set to a temperature T9, wherein 600° C.≤T9≤800° C.; wherein the melt is fed to the nozzle with a viscosity v, wherein 3 dPa·s≤v≤32 dPa·s to be transformed into droplets; or any combination thereof.

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise.

DETAILED DESCRIPTION OF THE INVENTION

Figure 1:
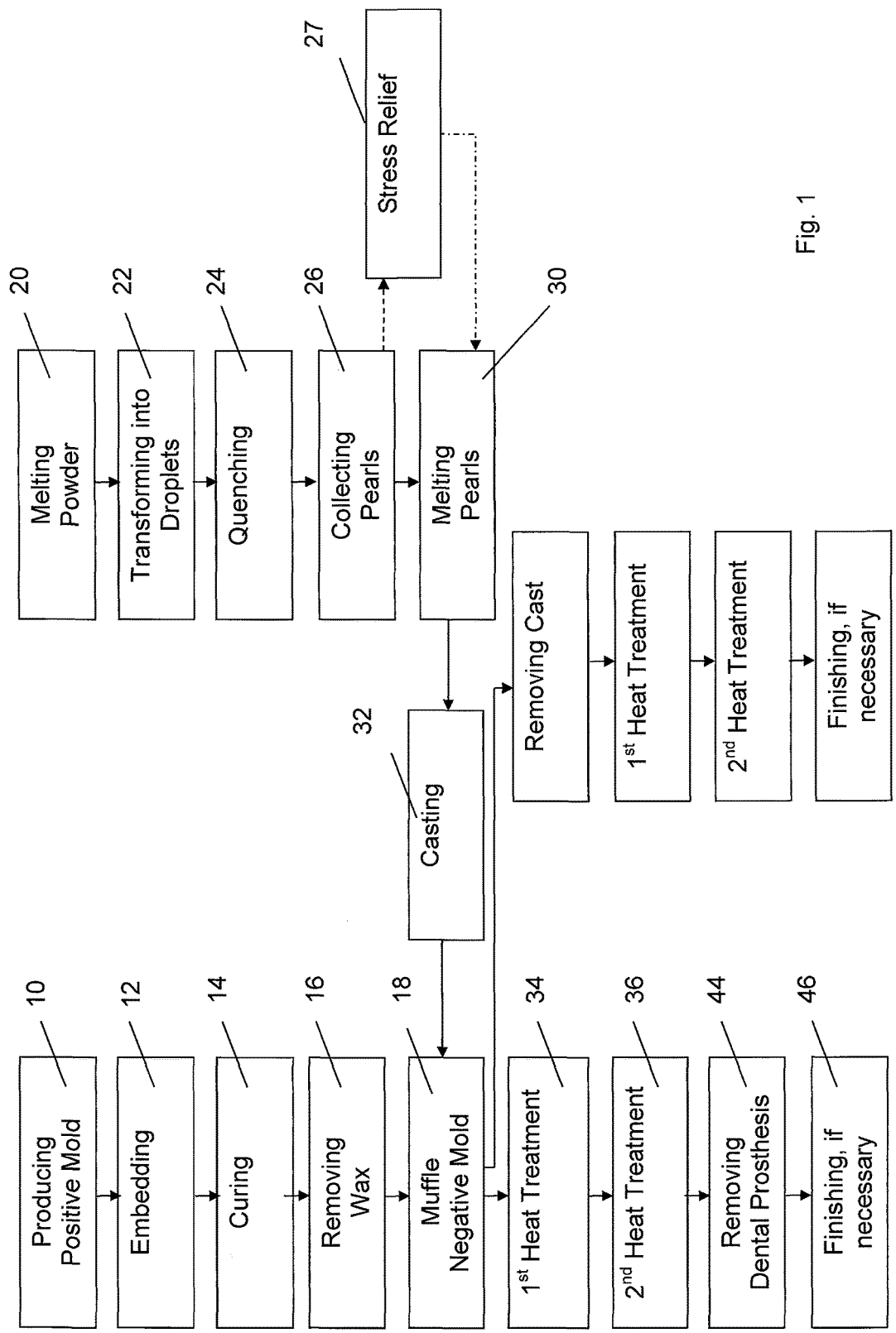
FIG. 1 is a flow-chart of one exemplary method of the present invention.

The invention relates to a method for producing a dental prosthesis based on lithium silicate glass or lithium silicate glass-ceramic, comprising at least the method steps of: melting a powder mixture containing at least $SiO_2$, $Li_2O$, $Al_2O_3$; and casting the thus produced melt or a melt made of the powder into a negative mold which is enclosed by an embedding compound and corresponds to the dental prosthesis to be produced.

Amongst others, to solve the problem, it is provided: melting a powder with a composition in wt-%

| | |
|---|---|
| $SiO_2$ | 50-70%; |
| $Li_2O$ | 5-25%; |
| $Al_2O_3$ | 0.1-20%; |
| $K_2O$ | 0.1-15%; |
| $CeO_2$ | 0.1-15%; |
| $B_2O_3$ | 0-5%; |
| $P_2O_5$ | 0-15%; |
| $Tb_2O_3$ | 0-2%; |
| $ZrO_2$ | 0-15%; |
| $ZnO_2$ | 0-4%; | and at least one additive between 0.1 and 5% of an oxide selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$; producing spherical, lens-shaped or rod-shaped glass particles solidified from the melt; portioning glass particles and filling them into a crucible; melting the glass particles in the crucible and setting a viscosity v, wherein 4 dPa·s≤v≤80 dPa·s; casting the thus produced melt into the negative mold which is enclosed by an embedding compound and corresponds to the dental prosthesis; solidifying the melt in the negative mold, and crystallizing lithium disilicate from the solidified melt by employing at least one heat treatment step at a temperature between 700° C. and 900° C.

In particular, the invention provides that the dental prosthesis is produced by centrifugal casting or vacuum die-casting.

Preferably, the invention is characterized in that the melt is cast with a viscosity v, wherein 9 dPa·s to 40 dPa·s.

To solve the problem, the invention essentially also provides that the dental prosthesis is produced using centrifugal casting or vacuum die-casting from the melt with the composition in wt-%:

| | |
|---|---|
| $SiO_2$ | 50-70%; |
| $Li_2O$ | 5-25%; |
| $Al_2O_3$ | 0.1-20%; |
| $K_2O$ | 0.1-15%; |
| $CeO_2$ | 0.1-15%; |
| $B_2O_3$ | 0-5%; |
| $P_2O_5$ | 0-15%; |
| $Tb_2O_3$ | 0-2%; |
| $ZrO_2$ | 0-15%; |
| $ZnO_2$ | 0-4%; | and at least one additive between 0.1% and 5% of at least one oxide selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$.

It is particularly provided that the composition additionally contains at least one oxide of a transition metal with an atomic number between 41 and 79, such as La, Nb, and Ta, with a wt-% proportion between 0 and 8%. The wt-% proportion of an oxide of the transition metals with the atomic number 59, 62, 64, 68 is at most 5%.

Preferably, for producing dental prosthesis a composition in wt-% is used, with:

| | |
|---|---|
| $SiO_2$ | 55-65%; |
| $Li_2O$ | 10-20%; |
| $Al_2O_3$ | 0.2-15%; |
| $K_2O$ | 0.2-10%; |
| $CeO_2$ | 0.1-10%; |
| $B_2O_3$ | 0-5%; |
| $P_2O_5$ | 1-10%; |
| $Tb_2O_3$ | 0-2%; |
| $ZrO_2$ | 2-15%; |
| $ZnO_2$ | 0-2%; | and at least one additive between 0.1% and 5% of oxides selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$, wherein it is particularly provided that the composition contains at least one oxide of a transition metal with an atomic number between 41 and 79, such as La, Nb, and Ta, with a wt-% proportion between 0% and 8%. The wt-% proportion of an oxide of the transition metals with the atomic number 59, 62, 64, 68 is at most 5%.

More preferably, for producing the dental prosthesis a composition in wt-% is used, with:

| | |
|---|---|
| $SiO_2$ | 57-63%; |
| $Li_2O$ | 11-19%; |
| $Al_2O_3$ | 0.5-10%; |
| $K_2O$ | 0.5-10%; |
| $CeO_2$ | 0.1-10%; |
| $B_2O_3$ | 0-5%; |
| $P_2O_5$ | 1-10%; |
| $Tb_2O_3$ | 0-2%; |
| $ZrO_2$ | 4-15%; |
| $ZnO_2$ | 0-2%; | and as well as at least one additive between 0.1% and 5% consisting of oxides from the group BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$, wherein it is particularly provided that the composition additionally contains at least one oxide of a transition metal with an atomic number between 41 and 79, such as La, Nb, and Ta, with a wt-% proportion between 0 and 6%. The wt-% proportion of an oxide of the transition metals with the atomic number 59, 62, 64, 68 is at most 5%.

Even more preferably, for producing the dental prosthesis a composition in wt-% is used, with:

| | |
|---|---|
| $SiO_2$ | 58-62%; |
| $Li_2O$ | 13-19%; |
| $Al_2O_3$ | 1-6%; |
| $K_2O$ | 1-5%; |
| $CeO_2$ | 0.1-5%; |
| $B_2O_3$ | 0-4%; |
| $P_2O_5$ | 2-8%; |
| $Tb_2O_3$ | 0-2%; |
| $ZrO_2$ | 8-12%; |
| $ZnO_2$ | 0-1%; | and at least one additive between 0.1% and 4% of oxides selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$, wherein it is particularly provided that the composition additionally contains at least one oxide of a transition metal with an atomic number between 41 and 79, such as La, Nb, and Ta, with a wt-% proportion between 0% and 5%. The wt-%-proportion of an oxide of the transition metals with the atomic number 59, 62, 64, 68 is at most 4%.

Based on the idea of the invention, the melt produced from the powder mixture is transformed into droplets so that the thus produced droplets fall through a cooling section, in which at least a superficial solidification of the droplets takes place, and that after falling through the cooling section and, if necessary, after being quenched, the droplets are fed to a receptacle which preferably contains a liquid, such as water or a high temperature cotton.

By using these measures, uniform spherical or lens-shaped solidified tail droplets are obtained, which are then melted prior to the casting.

Thus, a starting product for the casting is provided, which can be handled without difficulties. A filling of the crucible for the dental-technical casting is, depending on mass and seize of the object to be cast, respectively (for instance dental crown, dental bridge, abutment, etc.), possible to the desired extent without any difficulties.

To melt the powder mixture, it is provided that the powder mixture is subjected to a temperature T1, wherein 1500° C.≤T1≤1600° C. over a time t1, wherein 4 h≤t1≤12 h. The melting takes place in a suitable crucible made of Pt alloys, for example Pt/Rh 80/20, in which also the degassing takes place. The thus produced melt, i.e., the glass, is then fed to a nozzle which can be heated separately. The temperature T2 of the nozzle should be within the range between 1250° C. and 1450° C. Then, the hot liquid glass is released droplet by droplet from the nozzle. For this, the nozzle can be caused to vibrate. Irrespective thereof, the temperature T2 should be set to 1250° C.≤T2≤1450° C.

The droplets escaping from the nozzle are then falling through a cooling section, in which at least a superficial solidification takes place. This is necessary, as afterwards, the droplets preferably impinge on a sheet metal element such as sheet metal which can have a temperature between room temperature and 500° C. By impinging on the metal element, the droplets are flattened and diverted into a receptacle, which preferably is lined with high temperature cotton or consists of a container filled with water.

The droplets can be fed from the metal element via, for example, an inclined surface to the high temperature cotton and the water, respectively.

The shape of the solidified droplets can be described as a sphere, which is flattened on the bottom side, as a "semi-sphere" or as a "lens", respectively. The size of the droplets amounts to 2 mm to 9 mm at the equatorial diameter, with a distribution of +/−0.1 mm to +/−1 mm. The height of the "semisphere" is between 1 mm and 5 mm.

To release possible inner tensions that might have been caused by solidification and quenching, respectively, the droplets can be cooled down step-by-step in a stress-relieving oven from a temperature T3, wherein 350° C.≤T3≤500° C., particularly T3 being approximately 450° C. to room temperature over a time t3, wherein 2 h≤t3≤6 h.

During the dental-technical processing of cast dental prostheses, it is suggested precipitating crystalline phases in the glass to obtain the necessary strength. It is suggested that the melt solidified in the negative mold, i.e., the glass in the negative mold, is subjected to a heat treatment. Then, for example, lithium metasilicate can be precipitated during a first heat treatment at a temperature T4, wherein 600° C.≤T4≤760° C. over a time t4, wherein 20 min≤t4≤2 h.

Furthermore, the invention is alternatively characterized in that after solidification of the melt, the cast is removed from the embedding compound and then the cast is being subjected to a first heat treatment over a time t5, wherein 20 min≤t5≤120 min at a temperature T5, wherein 600° C.≤T5≤760° C., during which lithium metasilicate is formed as main crystalline phase.

In a second heat treatment that can likewise be carried out within the negative mold or after the demolding, and during which lithium disilicate is precipitated as main crystalline phase, the cast can be subjected to a heat treatment over a time t6, wherein 5 min≤t6≤60 min at a temperature T6, wherein 760° C.≤T6≤860° C.

The proportion of the crystalline phase of the lithium disilicate after respective heat treatments is 20 vol % to 90 vol % of the glass-ceramic.

Then, the lithium disilicate glass-ceramic is cooled down to room temperature over a time t7, wherein 10 min≤t7≤180 min.

It is particularly provided that a gypsum-bound embedding compound is used in which the negative mold is formed as known, like in a muffle system. A phosphate-bound embedding compound may also be used.

The advantage of a gypsum-bound embedding compound is that the mold can be removed without difficulties, as the embedding compound is soluble in water, for instance.

The crucible should be a ceramic crucible or a graphite crucible. The latter should be coated, for example, with boron nitride on the inside (for example as engobe), to prevent carbon and other crucible impurities, respectively, from contaminating the melt.

To melt the droplets the crucible is heated to a temperature T8, wherein 1200° C.≤T8≤1300° C., wherein during the casting process, the embedding compound in the section of the negative mold should be set to a temperature T8, wherein 600° C.≤T8≤800° C. At temperatures higher than 710° C. phosphate-bound embedding compounds have to be used.

Irrespective thereof, for casting the melt in the crucible should be set to a viscosity v, wherein 4 dPa·s≤v≤80 dPa·s, preferably 9 dPa·s≤v≤40 dPa·s. To produce a dental prosthesis by casting, the main procedural steps described in the following have to be carried out, which can also be learned from the flow-chart according to FIG. 1.

At first, a positive mold of the dental prosthesis is modeled by hand or rapid prototyping procedure, for example from wax or plastic (method step 10). The thus produced positive mold is, like in common muffle systems, embedded in an embedding compound, which is particularly gypsum-bound. Then, the embedding compound is cured and subsequently removed by heating the positive mold (method step 16) so that a cured embedding compound, i.e., a muffle, with an integrated negative mold is provided (method step 18). Irrespective thereof, for producing a lithium silicate glass a powder is melted (method step 20), which can have the following preferred composition:

| | |
|---|---|
| $SiO_2$ | 50-70%; |
| $Li_2O$ | 5-25%; |
| $Al_2O_3$ | 0.1-20%; |
| $K_2O$ | 0.1-15%; |
| $CeO_2$ | 0.1-15%; |
| $B_2O_3$ | 0-5%; |
| $P_2O_5$ | 0-15%; |
| $Tb_2O_3$ | 0-2%; |
| $ZrO_2$ | 0-15%; |
| $ZnO_2$ | 0-4%; | and
at least one additive between 0.1 and 5% of oxides selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$.

It is particularly provided that the composition contains at least one oxide of a transition metal with an atomic number between 41 and 79, such as La, Nb, and Ta, with a wt-% proportion between 0 and 8%. The wt-% proportion of an oxide of the transition metals with the atomic number 59, 62, 64, 68 is at most 5%.

Particularly, a composition is used, consisting of:

| | |
|---|---|
| $SiO_2$ | 55-65%; |
| $Li_2O$ | 10-20%; |
| $Al_2O_3$ | 0.2-15%; |
| $K_2O$ | 0.2-10%; |
| $CeO_2$ | 0.1-10%; |
| $B_2O_3$ | 0-5%; |
| $P_2O_5$ | 1-10%; |
| $Tb_2O_3$ | 0-2%; |
| $ZrO_2$ | 2-15%; |
| $ZnO_2$ | 0-2%; | and at least one additive between 0.1 and 5% of oxides selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$, wherein it is particularly provided that the composition additionally contains at least one oxide of a transition metal with an atomic number between 41 and 79, such as La, Nb, and Ta, with a wt-% proportion between 0 and 8%. The wt-% proportion of an oxide of the transition metals with the atomic number 59, 62, 64, 68 is at most 5%.

Preferably, the composition is to be selected as follows:

| | |
|---|---|
| $SiO_2$ | 57-63%; |
| $Li_2O$ | 11-19%; |
| $Al_2O_3$ | 0.5-10%; |
| $K_2O$ | 0.5-10%; |
| $CeO_2$ | 0.1-10%; |
| $B_2O_3$ | 0-5%; |
| $P_2O_5$ | 1-10%; |
| $Tb_2O_3$ | 0-2%; |
| $ZrO_2$ | 4-15%; |
| $ZnO_2$ | 0-2%; | and at least one additive between 0.1 and 5% of oxides selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$, wherein it is particularly provided that the composition additionally contains at least one oxide of a transition metal with an atomic number between 41 and 79, such as La, Nb, and Ta, with a wt-% proportion between 0 and 6%. The wt-% proportion of an oxide of the transition metals with the atomic number 59, 62, 64, 68 is at most 5%.

Particularly preferably, the following composition is to be selected:

| | |
|---|---|
| $SiO_2$ | 58-62%; |
| $Li_2O$ | 13-19%; |
| $Al_2O_3$ | 1-6%; |
| $K_2O$ | 1-5%; |
| $CeO_2$ | 0.1-5%; |
| $B_2O_3$ | 0-5%; |
| $P_2O_5$ | 2-8%; |
| $Tb_2O_3$ | 0-2%; |
| $ZrO_2$ | 8-12%; |
| $ZnO_2$ | 0-1%; | and at least one additive between 0.1 and 4% of oxides selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$, wherein it is particularly provided that the composition additionally contains at least one oxide of a transition metal with an atomic number between 41 and 79, such as La, Nb, and Ta, with a wt-% proportion between 0 and 5%. The wt-% proportion of an oxide of the transition metals with the atomic number 59, 62, 64, 68 is at most 4%.

Glass coloring oxides can also be components of the additives.

Irrespective of the type of the composition, it has to be mentioned that the total percent-ages by weight of the components of the powder mixture yield 100 wt-% in each composition with the given components.

The powder mixture is melted and refined in a crucible, particularly consisting of a high-temperature resistant platinum alloy, such as for example Pt/Rh 80/20, or Pt/Rh 90/10 dispersion reinforced, over a time t1 between 4 h and 12 h at a temperature T1 between 1500° C. and 1600° C., in particular over a time of 4 h at a temperature of 1540° C. The thus produced glass is then preferably transformed into droplets (method step 22). The glass is fed to a preferably vibrating nozzle, which has a temperature T2 between 1250° C. and 1450° C., in particular 1310° C. The glass escapes from the nozzle in the shape of droplets. When the melt is transformed into semispheres, a viscosity of the melt of preferably 3 dPa·s to 32 dPa·s has to be set. The nozzle diameter is 2.0 mm to 3.0 mm, preferably 2.6 mm, the length of the nozzle is preferably 10 mm to 40 mm, and the oscillation frequency of the nozzle is between 40 Hz and 60 Hz, preferably 50 Hz.

The droplets are at least superficially pre-solidified when falling through a cooling section to then impinge on a metal element, such as a sheet metal, which should have a temperature between room temperature to 500° C., particularly in the range of room temperature to 100° C. Due to this, the droplets are quenched (step 24). The quenched droplets are then fed to a container (step 26), which can, for example, contain high temperature cotton or water. So-called pearls are formed, i.e., spherical or lens-shaped droplets, which have almost equal dimensions due to the conducted method. Preferably, nozzle section, temperature of the metal element, temperature of the nozzle and temperature of the hot glass are matched to each other so that the following dimensions arise for the pearls: main diameter R, wherein 2 mm R 9 mm and height H, wherein 1 mm≤H≤5 mm.

Figure 3:
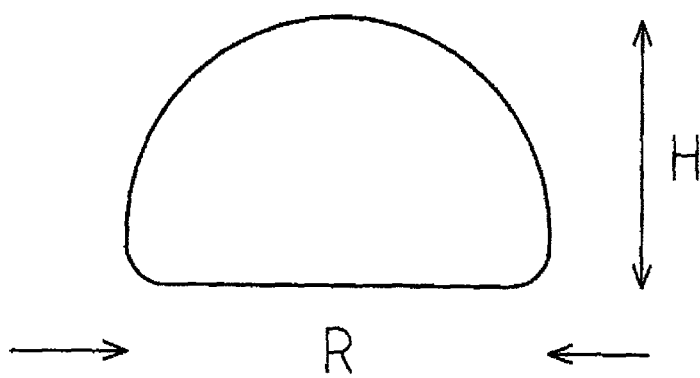
FIG. 3 is a zoomed in view of one exemplary droplet shown in FIG. 2.

A cross-section of a respective pearl or droplet is shown in FIG. 3. The cross-section illustrates that one could actually refer to a roll shape with a smooth surface.

Then, the pearls are melted (step 30). For this, particularly a crucible made of graphite or ceramic is used. When using a graphite crucible, is should be coated. For this, boron nitride can be used (or a crucible completely made of silicon carbide and boron nitride, respectively). By applying this measure, it is ensured that carbon cannot penetrate into the melt. Preferably, the crucible has the shape of a closed hollow cylinder, in the front side of which an opening is located in the center, having a diameter of preferably 8 mm.

Then, in step 32, the negative mold in the muffle is filled with the lithium silicate glass melt in a casting process. Preferably, centrifugal casting or vacuum die-casting procedures are used, which are at the time being only used for alloy castings, particularly for alloys containing precious metals or base metal alloys, which are based on cobalt chromium or nickel chrome. Suitable arrangements are, for example, described in DE 31 17 470 (centrifugal casting)

and DE 26 51 842 (vacuum die-casting), respectively. The parameters to be considered in this are the following:

Centrifugal Casting:
Temperature of the melt: 1230° C. After the filling of the muffle follows an after running of the crucible and the muffle between 5 min and 15 min, while the muffle is still being rotated. Afterwards, the muffle can either be tempered in a preheater (for example at 600° C.) or cooled down to room temperature by being left on a suitable unheated and heat-resistant support.

Vacuum Die-Casting:
Temperature of the melt during the casting: 1250° C. with a casting time of 5 min (i.e., for this time, crucible and muffle remain in the casting position). Then, the muffle is cooled down in the casting machine to 600° C.

Before fusing the pearls, a further method step can be conducted to reduce tensions that arose during the quenching (step 27). For this, the pearls can be heated to a temperature T3 of approximately 450° C. in a stress-relieving oven, and then be cooled down step-by-step to room temperature within a time t3 of 2 h to 6 h.

The muffle with the solidified cast forming the dental prosthesis can then be subjected to a first heat treatment; over a time t4 of 30 min and 120 min a pre-crystallization takes place at a temperature T4 between 600° C. and 760° C., with lithium metasilicate as main crystalline phase (method step 34). Then, the muffle can remain in the preheater to form lithium disilicate as main crystalline phase, wherein a temperature T6 is set between 760° C. and 860° C. over a time t6 of 5 min to 20 min. Due to this, lithium disilicate crystals are formed (method step 36).

Alternatively, the cast can be removed from the muffle (method step 38) and be subjected to the first and second heat treatment in an oven (method steps 40, 42) as described before. Temperature T5 and time t5 can be selected according to T4 and t4.

If the crystallization takes place in the muffle, the dental prosthesis is removed in method step 44 and then, to the extent required, finished by blasting with sand particles (method step 46). A respective finishing (step 48) can also take place after the second heat treatment step 42.

Dental prostheses manufactured in such a manner have the following properties:

Bending strength between 200 MPa and 400 MPa (according to DIN ISO 6872:2008). Translucency for visible light of 30-60% (transmittance measurement) at a thickness of 3 mm and a dentoid elementary color (according to VITA classical shade guide~A1~A2). Acid solubility according to ISO 68772:2008 below 100 μg/cm².

Figure 2:
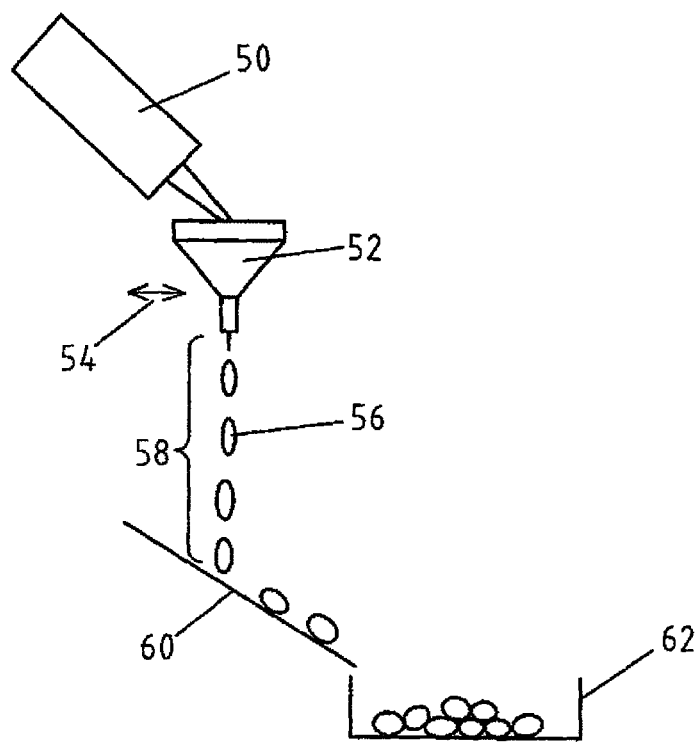
FIG. 2 is a perspective view of at least one step of the exemplary method shown in FIG. 1 showing a formation of droplets.

The manufacture of the pearls, i.e. droplets, which have a spherical or lens-shaped geometry, with a flattening at the bottom side, is in principle shown in FIG. 2. A crucible is labeled with 50, the initial powder mixture is filled into the crucible and melted over the time t1 between 4 h and 12 h at the temperature T1 between 1500° C. to 1600° C. and subsequently degassed. The melt is fed to a nozzle 52, which can be excited to vibrate (double arrow 54). The melt escapes from the nozzle 52 in a droplet-shaped manner (droplet 56); after a cooling section 58, the droplets fall onto a sheet metal 60. Within the cooling section 58, the droplets 56 solidify at least superficially to such an extent that when impinging on the sheet metal 53, mostly a droplet shape is maintained. The sheet metal 60, which is set to a temperature between room temperature and 500° C., causes a quenching of the droplets 56. Starting from the sheet metal 60, the surface of which runs inclined to the falling direction of the droplets 48, the droplets reach a receptacle 62, which can be filled with water or, for instance, with high temperature cotton. Subsequently, the cured droplets which are referred to as pearls are removed from the receptacle 62 and, if necessary, fed to a stress-relieving oven to reduce stress, as described above. Then, the pearls are melted as described above to produce a dental prosthesis in the casting process.

Further details, advantages and features of the invention do not only result from the claims, their features—in insulation and/or in combination—but also from the description of preferred embodiments.

The invention claimed is:

1. A method for producing a dental prosthesis based on lithium silicate glass or lithium silicate glass-ceramic, comprising the steps of:
   (a) melting a powder mixture with the composition in wt-%

| | |
|---|---|
| $SiO_2$ | 50-70%; |
| $Li_2O$ | 5-25%; |
| $Al_2O_3$ | 0.1-20%; |
| $K_2O$ | 0.1-15%; |
| $CeO_2$ | 0.1-15%; |
| $B_2O_3$ | 0-5%; |
| $P_2O_5$ | 0-15%; |
| $Tb_2O_3$ | 0-2%; |
| $ZrO_2$ | 0-15%; |
| ZnO | 0-4%; | and
   at least one additive between 0.1 and 5 wt-%, the additive being selected from the group consisting of BaO, CaO, MgO, MnO, $Er_2O_3$, $Gd_2O_3$, $Na_2O$, $Pr_2O_3$, $Pr_6O_{11}$, $Sm_2O_3$, $TiO_2$, $V_2O_5$, and $Y_2O_3$,
   (b) producing spherical or lens-shaped glass particles solidified from the melt;
   (c) portioning the glass particles and filling them into a crucible;
   (d) melting the glass particles in the crucible and setting a viscosity v, wherein 4 dPa·s≤v≤80 dPa·s;
   (e) casting the thus produced melt into a negative mold which is enclosed by an embedding compound and corresponds to the dental prosthesis to be produced;
   (f) solidifying the melt in the negative mold;
   (g) crystallizing lithium metasilicate as main crystalline phase from the solidified melt by employing a first heat treatment at a temperature between 600° C. and 760° C. over a time between 20 min and 120 min, and
   (e) comprising the step of crystallizing lithium disilicate as main crystalline phase in a second heat treatment at a temperature between 760° C. and 860° C. over a time between 5 min and 60 min;
   wherein the first and second heat treatment of the solidified melt takes place either in the negative mold or after removal from the negative mold.

2. The method according to claim 1, wherein the dental prosthesis is produced by centrifugal casting or vacuum die-casting.

3. The method according to claim 1, wherein the melt is cast with a viscosity v, wherein 9 dPa·s to 40 dPa·s.

4. The method according to claim 1, wherein the melted powder is transformed into droplets by means of a nozzle, that the droplets are falling through a cooling section, in which at least a superficial solidification of the droplets takes place, that after falling through the cooling section the droplets are collected by a receptacle containing a liquid or a high temperature cotton, if necessary after quenching them beforehand.

5. The method according to claim 4, wherein for quenching, the droplets fall onto a metal substrate, the temperature of which is set between room temperature and 500° C.

6. The method according to claim 4, wherein during the transformation of the droplets, the nozzle is set to a temperature T2, wherein 1250° C.≤T2≤1450° C.

7. The method according to claim 4, wherein during the transformation of the droplets, the nozzle is caused to vibrate at a frequency between 40 Hz and 60 Hz.

8. The method according to claim 4, wherein over a time t3, wherein 2 h≤t3≤6 h, the collected droplets are cooled down from a temperature T3, wherein 350° C.≤T3≤500° C. to room temperature to reduce internal stress.

9. The method according to claim 4, wherein the droplets are melted in a crucible or ladle made of graphite or ceramic.

10. The method according to claim 9, wherein when a graphite crucible is used, it is at least coated at the inside.

11. The method according to claim 1, wherein the powder mixture is melted over a time t1, wherein 4 h≤t1≤12 h at a temperature T1, wherein 1500° C.≤T1≤1600° C.

12. The method according to claim 1, wherein after the second heat treatment, the cast is cooled down to room temperature over a time t7, wherein 10 min≤t7≤180 min.

13. The method according to claim 1, wherein a gypsum-bound embedding compound is used as an embedding compound.

14. The method according to claim 1, wherein the melt is fed to the negative mold with a temperature T8, wherein 1200° C.≤T8≤1300° C.

15. The method according to claim 1, wherein when casting the melt, the embedding compound is set to a temperature T9, wherein 600° C.≤T9≤800° C.

16. The method according to claim 1, wherein the melt is fed to the nozzle with a viscosity v, wherein 3 dPa·s≤v≤32 dPa·s to be transformed into droplets.

* * * * *